United States Patent [19]
Smith

[11] Patent Number: 5,832,774
[45] Date of Patent: Nov. 10, 1998

[54] SPRING TESTER

[76] Inventor: John Antony Smith, 7 South Road, Templefields, Harlow, Essex CM20 2AP, United Kingdom

[21] Appl. No.: 709,693

[22] Filed: Sep. 9, 1996

[30]     Foreign Application Priority Data

Sep. 8, 1995 [GB] United Kingdom .................. 9518406

[51] Int. Cl.$^6$ ....................................................... G01L 1/04
[52] U.S. Cl. .................................................. 73/161; 73/818
[58] Field of Search ........................................ 73/161, 818

[56]            References Cited

U.S. PATENT DOCUMENTS

| 1,251,556 | 1/1918 | Miller ......................................... 73/161 |
| 1,992,987 | 3/1935 | Bitzer et al. ............................... 73/161 |
| 2,035,029 | 3/1936 | Thomas ...................................... 73/161 |
| 2,472,545 | 6/1949 | Nixon ......................................... 73/161 |
| 3,638,486 | 2/1972 | Lambert ...................................... 73/161 |
| 3,881,348 | 5/1975 | Morton . |
| 3,918,301 | 11/1975 | Baer . |
| 4,157,033 | 6/1979 | Shereda et al. ............................ 73/161 |
| 4,559,820 | 12/1985 | Zava et al. . |
| 5,392,649 | 2/1995 | Yoo . |

FOREIGN PATENT DOCUMENTS

| 1368569 | 10/1974 | United Kingdom . |
| 2247956 | 3/1992 | United Kingdom . |

*Primary Examiner*—Max H. Noori
*Attorney, Agent, or Firm*—Harness, Dickey & Pierce, P.L.C.

[57]           ABSTRACT

A spring tester has a hydraulic ram which urges a bearer plate towards a load cell to achieve a predetermined fixed spacing D between them. A replaceable spacer allows adjustment of the distance D to a distance d. A spring to be tested is compressed to the length d and the load indicated by the load cell. Under test, the spring is laid in a cylindrical channel in a carriage to simulate the operation of the spring in an aircraft braking system.

7 Claims, 2 Drawing Sheets

SPRING TESTER

The present invention relates to a device for testing springs, and in particular for measuring the load/compression characteristics of a spring to enable matching of springs.

Manufacturers require a certain spring load at a predetermined (compressed) spring length.

The device is particularly suited to testing springs for aircraft braking systems, but may have other uses.

In aircraft brakes, the braking discs are released by helical springs, and urged together hydraulically for braking, With composite type braking discs, in particular, the clearance between the discs (when the brake is off) is relatively small, If the springs are not evenly matched the discs can be misaligned—leading to grabbing. This in turn can result in wearing flat spots on the aircraft tires.

Traditional spring testers compress the spring between two horizontal platens and measure the load vs compression. These devices are expensive, slow to operate and, we have found, do not accurately reflect the spring performance when it is in use in the aircraft braking system. In such braking systems, the spring lays horizontally in a guide tube. We have found that the spring coils bear on the wall of the tube when compressed and this affects the spring performance. Moreover, the spring performance varies according to the rotational orientation of the spring. It is thought that this is due to the asymmetric nature of the end coils of the spring, which causes the spring to bow and bear against the channel wall when compressed, but other factors may be involved.

The present invention provides a device for testing a helical spring, comprising means for compressing the spring by a predetermined amount, and means for measuring the load on the spring when compressed. The spring is preferably compressed by a ram which moves a constant distance, and a load cell is provided at one end of the spring to measure the spring force or load, when compressed by the ram. The ram may be hydraulically operated.

The spring is preferably laid in a horizontal channel. In this way the spring testing environment simulates the working environment of the spring.

Preferably the ram urges the spring against a load cell and the distance between the load cell and ram is constant when the ram is fully extended, To enable testing of springs of different length, spacers of predetermined length are provided in line with the spring. Thus, the spacer will determine the final, compressed length of the spring.

The device of the invention is very simple in construction and operation and so well suited to use in assembly operations and repair/maintenance shops for testing springs prior to installation.

The invention will be further described by way of example with reference to the accompanying drawings, in which.

Figure 1A:
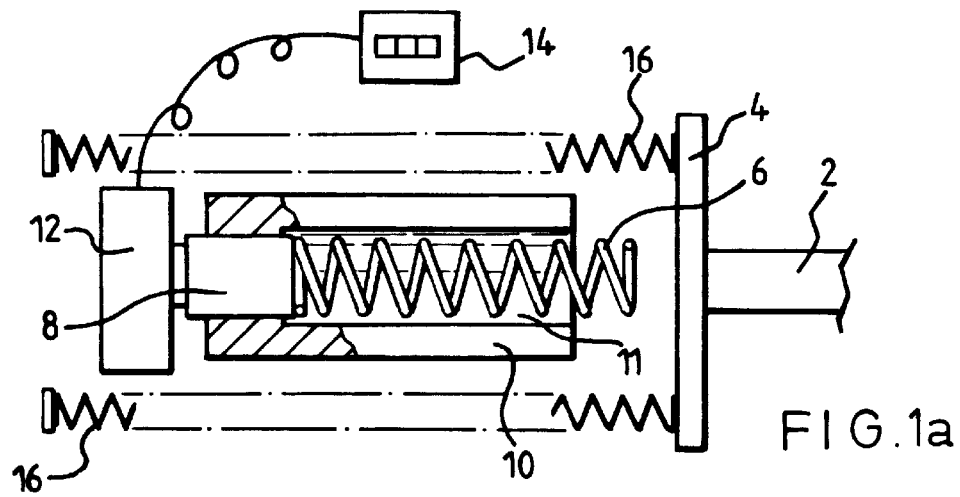
FIGS. 1a and 1b illustrate schematically the structure and operation of a device according to the invention.
Figure 1B:
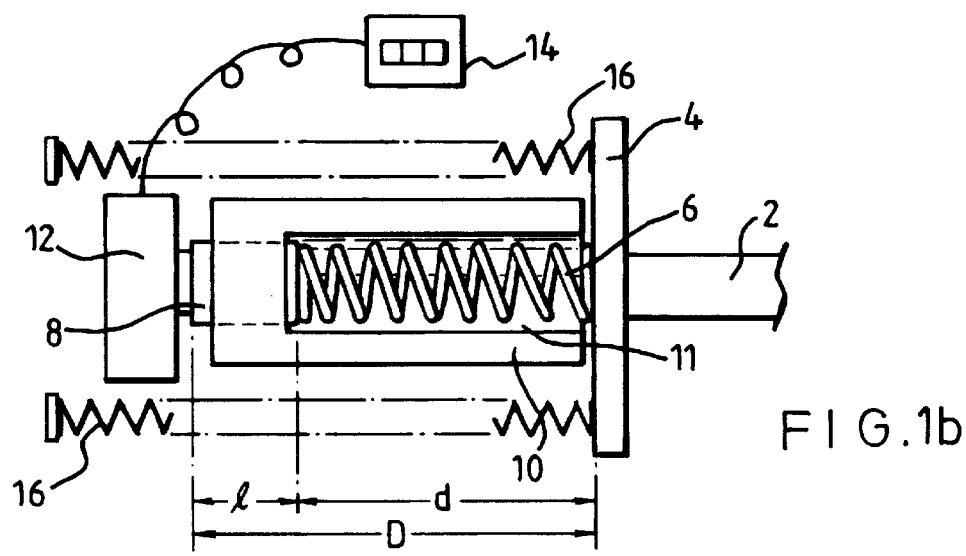

Referring to FIGS. 1a and 1b, a spring testing device in accordance with the invention has a hydraulically actuated ram 2 which acts through a bearer plate 4 to compress a spring 6 against a steel slug 8. The slug 8 to carried by a sliding carriage 10 which has an arcuate, semi-cylindrical channel 11 to loosely receive the spring 6.

Preferably the radius of the channel 11 is similar to the radius of the channel in which the spring is housed in use.

The slug 8 bears on a load cell 12 providing an output to a digital meter 14.

In use the one-way ram 2 is pushed back to its fullest extent by the operation of springs 16. A spring 6 to be tested is positioned in the carriage 10 between the slug 8 and plate 4, and the ram 2 is then actuated to compress the spring 6. The ram moves to its fullest extent, or some other datum point, giving a predetermined spacing D between the bearer plate 4 and the load cell 12. Thus, with a slug 8 of predetermined length l, the compressed length d of the spring is known. The load on the spring, when compressed is then output by the load cell 12.

Typically a manufacturer will provide springs of 120 mm length, and will want the spring load to be a particular value, say 1,000 lbs, when compressed to an exact length of 105 mm.

To cater for springs of different length, and hence of different compressed length d, the slug 8 is changed. Conveniently the slug 8 is fixed in the carriage 10 and the slug and carriage are changed as a single unit.

It has been found that the spring load depends on the orientation of the spring in the carriage 10. As the spring is rotated by intervals about its axis, different test results are obtained, varying by as much as 50 lbs in 1,000 lbs. This is believed to be caused by the spring deforming off-axis, so that the coils bind against the surface of the channel 11. This could be avoided by raising the spring away from the channel wall. Also the use of floppy feet on the bearer plate 4 and slug 8 to bear on the spring ends may provide more even loading of the spring.

It is believed that this situation also pertains when the spring is in use in an aircraft brake. Thus, it may be desirable to ensure that a spring is located in a particular orientation in the aircraft brake, and to simulate this orientation in the test device, or vice versa.

The carriage 10 is of alloy with the surface of the channel 11 hard anodised to prevent scuffing by the spring coils.

Figure 2:
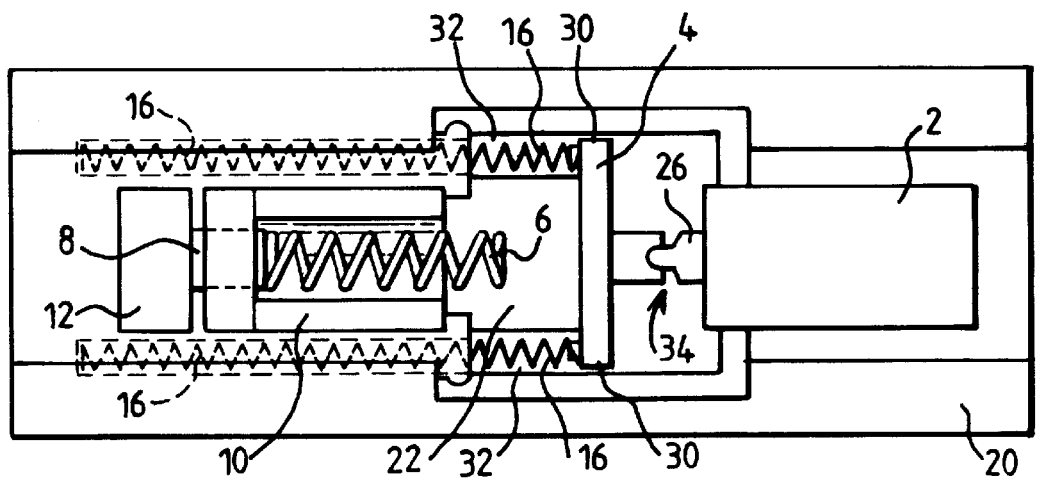
FIG. 2 is a plan view of part of a device according to the invention.

FIG. 2 shows in plan view an embodiment of a spring testing device in accordance with the invention.

A frame 20 has a central channel 22 housing at one end a hydraulic ram 2, which is fed from an external supply (not shown). The ram piston 26 carries a bearer plate 4 which is guided at its outer ends 30 by shelves 32 in the channel wall. The piston 26 is connected to the bearer plate 4 by a floppy foot or ball and socket joint 34 to allow the plate 4 to align with the end of the spring 6. Springs 16 urge the bearer plate 4 and piston 26 back to the unextended position, so that a single acting ram 2 can be used.

The opposite end of the channel 22 houses a load cell 12.

Figure 4:
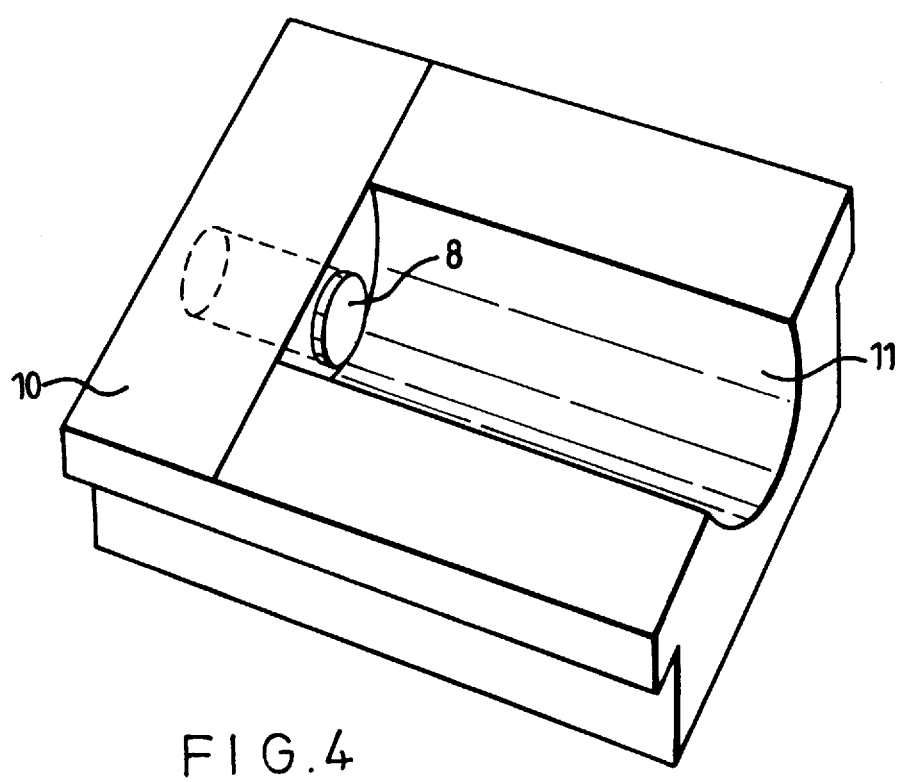
FIG. 4 is an enlarged perspective view of a carriage of the device of FIG. 2.

A carriage 10, shown in perspective in FIG. 4, slides in the channel 22, and houses a slug 8 at one end. Slug 8 bears on the sensor of the load cell 12. A spring to be tested rests in a semi-cylindrical arcuate channel 11 in the carriage 10.

In operation, with the piston 26 retracted, a carriage having a slug 8 and a channel 11 of the appropriate dimensions for the springs to be tested, is selected and placed in the channel 22. A spring 6 is placed in the channel 11.

Figure 3:
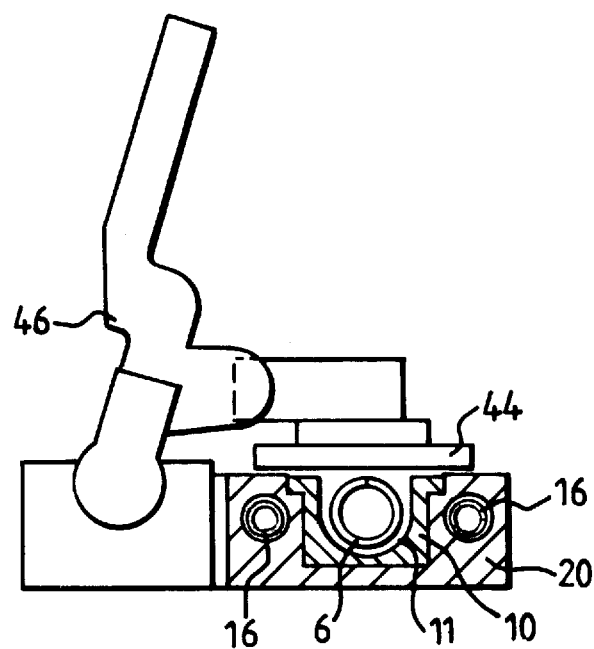
FIG. 3 is an end view of the device of FIG. 2, partly cut away, showing a closure mechanism.

A cover 44 (FIG. 3) is brought down over the carriage 38 and channel 22 by an over-contre lever mechanism 46. This triggers a switch (not shown) which actuates the ram 2. Piston 26 extends to its full extent to compress the spring to a predetermined length set by the distance between the bearer plate 4 and the end of the slug 8 on which the spring 6 bears.

In practice, it is desirable to rotate the spring about its axis, testing It at several orientations. The spring can be marked to allow indication of the test load at different orientations.

The realisation that the test load is dependent on the rotational orientation of the spring in the channel 11, also indicates that an improvement in aircraft brake operation may be achieved if this factor is taken into account: for example by ensuring that the springs 6 are held in a predeternined orientation in their guide channels, or by holding the spring 6 clear of the channel wall.

To stimulate more closely the performance of the spring 6 in use, the channel 11 may be completely cylindrical.

I claim:

1. A device for testing a helical spring, comprising:

a carriage;

an elongated channel defined by the carriage, the channel being horizontally oriented when the device is in use, the channel having a surface on which the spring rests;

means for compressing the spring to a predetermined length when the spring is resting on the surface of the channel; and means for measuring the load on the spring when the spring is compressed to the predetermined length.

2. A device as claimed in claim 1, comprising a ram for compressing the spring against a stop, the ram moving to a predettmined distance from the stop, and a replaceable spacer in line with the spring for pre-setting the compressed length of the spring.

3. A device as claimed in claim 1, comprising a load cell for measuring the load on the spring.

4. A device for testing the load on a spring for an aircraft braking system, comprising:

a carriage, the carriage having a horizontally oriented channel for receiving the spring, the channel having a surface on which the spring rests, the spring having a first end and a second end;

a plug, the plug having a first end and a second end, the plug being located at one end of the channel;

a load cell, the first end of the plug bearing on the load cell, the first end of the spring bearing on the second end of the plug; and a ram, the ram bearing on the second end of the spring, the ram being extendable towards the plug to compress the spring to a predetermined length measured between the ram and the second end of the plug.

5. A device as claimed in claim 4, In which the load cell and the ram are mounted on a frame, and the channel is provided in a carriage which is slidable in the frame between the rain and the load cell.

6. A device as claimed in claim 5, in which the plug is housed in an end wall of the carriage.

7. A device as claimed in claim 6, in which, in use, the compressed length of the spring is longer than the channel in the carriage.

* * * * *